(12) United States Patent
Kuhn

(10) Patent No.: US 6,351,217 B1
(45) Date of Patent: Feb. 26, 2002

(54) CLINICAL THERMOMETER

(75) Inventor: Jens Kuhn, Ilmenau (DE)

(73) Assignee: Geratherm Medical AG, Geschwenda (DE)

( * ) Notice: Subject to any disclaimer, the term of this patent is extended or adjusted under 35 U.S.C. 154(b) by 0 days.

(21) Appl. No.: 09/654,351

(22) Filed: Sep. 1, 2000

(30) Foreign Application Priority Data

Sep. 3, 1999 (DE) .......................................... 199 42 089

(51) Int. Cl.[7] .............................................. G08B 23/00
(52) U.S. Cl. .................................. 340/573.1; 340/573.7
(58) Field of Search .......................... 340/573.1, 573.7, 340/584; 600/301, 474, 484

(56) References Cited

U.S. PATENT DOCUMENTS

| | | | |
|---|---|---|---|
| 4,636,093 A | | 1/1987 | Nagasaka et al. ............ 374/186 |
| 5,559,497 A | | 9/1996 | Hong ....................... 340/573.1 |
| 5,653,239 A | * | 8/1997 | Pompie et al. .............. 600/474 |
| 5,724,025 A | * | 3/1998 | Tavori ..................... 340/573.1 |
| 6,030,342 A | * | 2/2000 | Amano et al. .............. 600/301 |

FOREIGN PATENT DOCUMENTS

| | | |
|---|---|---|
| DE | 298 04 222 U 1 | 10/1998 |
| EP | 0 424 102 A1 | 4/1991 |
| GB | 2 286 684 | 8/1995 |
| WO | WO 90/09570 | 8/1990 |

* cited by examiner

*Primary Examiner*—Van T Trieu
(74) *Attorney, Agent, or Firm*—Connolly, Bove, Lodge & Hutz LLP

(57) ABSTRACT

The invention relates to a clinical thermometer of a small design portable also by children, having a data memory 18 and an interface 21, by which both continually monitoring measurements and discontinued cyclic measurements as a maximum thermometer may be comfortably performed at locations which are medically established for measuring body temperature. Depending on the selected setting of the storage rate, the temperature of the measurement location is continuously monitored or cyclic individual measurements are taken. For changing the mode of operation, no extra keys or switches are necessary which would be difficult to place on a small, compact housing 14.

13 Claims, 3 Drawing Sheets

CLINICAL THERMOMETER

BACKGROUND OF THE INVENTION

Small children and babies are prone to suffer from colds and various infectious diseases, e.g. the so-called children's diseases (measles, smallpox, German measles, scarlet fever and the like). These diseases put considerable stress on the parents, also because of the necessity to check the child's body temperature regularly in order to recognise drastic changes at once. To this end, the parents at night have to interrupt their own sleep and that of their child, which is unpleasant for all concerned. It would therefore be desirable to have a thermometer which performs such monitoring function automatically, takes the body temperature continually and initiates an alarm when critical changes occur.

It is often not easy for the parents to decide whether a given temperature increase is dangerous for the child. It would thus be most advantageous if the detected temperature curve could be readily transmitted, e.g. by e-mail, to the family doctor who will use his expertise to judge the measurements and take appropriate steps.

Fever can become dangerous if it causes convulsions which may entrain a loss of conscience. Such convulsions are caused by a sudden increase in temperature. A convulsion of this type can occur specifically with children between the age of six months to five years. About 3 to 4 per cent of the children of this age are affected. As the duration of the attack increases, it enhances the risk of later afibrile effects, i.e. epilepsy. Therefore, optimum therapy is of the essence in an acute attack. Unless antispasmodic measures are taken within few minutes, the attack represents a genuine emergency.

To reduce the risk of occurring, specifically re-occurring, convulsions during fever, it is recommended to apply fever-reducing measures from a body temperature of 38.5° C. on as early as possible. Also in this case, a continually measuring thermometer is required which generates an alarm when a limit temperature is exceeded, to enable quick action. Since many of the endangered children are active, such a thermometer must be unproblematic to carry by children.

With older, specifically helpless persons, insufficient food intake, chronic infections and the like may cause emaciation (cachexia), which in turn may lead to dangerous hypothermia. A body temperature below about 30° C. may result in a state of unconsciousness making it impossible for the person to help himself or herself. A continually measuring thermometer, which generates an alarm when the temperature falls below a limit value, allows endangered persons to obtain quick help in acute cases.

A relatively dependable medication-free method of natural contraception is the temperature method in which a woman can determine the fertile days of her menstrual period by watching the basal temperature. Another important parameter in diagnosing and curing disturbances of the menstrual period is the wake-up temperature. The recordal and evaluation of the basal temperature requires a thermometer which operates as a maximum thermometer. The temperature of the measurement location is detected until the rising gradient reaches or falls below a limit value. This type of thermometer will always give only the largest temperature value found in a given measuring period, i.e. the maximum. A cyclo-thermometer may be in the form of a maximum thermometer which stores the temperature maximum along with the time and a day number and upon request displays this information or transmits it to a personal computer.

A plurality of suggestions have been made for continuously monitoring the body temperature, particularly of small children; compare DE 298 04 222 U1, U.S. Pat. No. 5,559,497, FR 26 94 977 A1, WO 90/09570, DD 254 643 A and GB 2 286 684 A. These thermometers, however, have no maximum function and are therefore unsuited for taking individual measurements.

Many documents propose to fix a thermometer to the wrist; compare U.S. Pat. No. 5,559,497, FR 26 94 977 A1 and GB 2 286 684 A. The wrist, however, is unsuited for taking continuously monitoring body temperature measurements, since the measurement results may very strongly depend on the surrounding temperature and on the location of measurement being covered (such as by clothing, a blanket, position of the wrist underneath the body). The calibration of the thermometer with respect to the body core temperature by means of a reference sensor, as provided in GB 2 286 684 A does not solve this problem since the calibration is valid for one given environmental situation only.

EP 0 424 102 A1 discloses a thermometer for women for daily determining the basal temperature. The thermometer operates as a maximum thermometer but is unsuited for taking continuously monitoring measurements.

U.S. Pat. No. 4,636,093 discloses a temperature measuring arrangement, by which temperature values detected at a number of locations by means of one or a plurality of radiation thermometers can be performed with a portable recording device and subsequently transmitted to a processing equipment. Each measurement is taken by manually operating the recording device and may represent the instant temperature or the maximum value that occurs within a short period.

SUMMARY OF THE INVENTION

It is an object of the invention to provide a clinical thermometer which permits taking both continually monitoring measurements and discontinuous cyclic measurements as a maximum thermometer.

This object is met by a clinical thermometer having a housing, a temperature sensor connected to said housing, a measuring circuit disposed in said housing and including a micro controller and a data memory for recording the temperature value measured by said temperature sensor, said data memory having a storage rate, a voltage supply for powering said measuring circuit, and a mode switch for switching the storage rate of said memory between a continuous operation mode, in which the temperature of a measurement location is continuously monitored, and a discontinuous operation mode, in which individual temperature measurements are recorded.

The setting of storage rate determines whether the thermometer continously monitors the temperature of the measurement location or performs cyclic or individual measurements. For changing the mode of operation, no extra switch is required, which would be difficult to place on a small, compact housing.

The storage rate is adapted to be set to zero to switch-over to the discontinuous operation mode. For any storage rate different from zero, the thermometer operates as a continually measuring thermometer which regularly stores the actual temperature in a data memory at regular intervals in accordance with the selected storage rate. In the discontinuous operation mode, the thermometer preferably operates as a maximum thermometer.

Since the thermometer is to be used also with small children, any inadvertent switching-off or reconfiguration must be safely excluded. This is achieved by a safety switch which locks an on/off switch and the mode switch. The safety switch is preferably recessed with respect to the housing surface so that any inadvertent actuation is prevented.

The thermometer preferably includes a display to indicate, in the continously operation mode, the day of the uninterrupted measurement and, in the discontinuous mode, the number of measurements recorded.

In another preferred embodiment, the micro controller provides two independently adjustable alarm temperatures, and the thermometer further includes a signal generator adapted to be actuated by either one of the alarm temperatures. The signal generator may produce an acoustical and/or optical alarm.

For ensuring that the thermometer carries out its monitoring function, the micro controller preferably has means for automatically and periodically performing a reference measurement and actuating the signal generator when the result of the reference measurement deviates from a standard value. It may also have means for actuating the signal generator when the supply voltage falls below a critical value.

The temperature sensor is integrated in a flexible watertight cable connected to the housing. This permits the temperature sensor to be placed either on the inguen or in the axilla.

Means provided on the housing for receiving a mounting adapter further allows the thermometer to be mounted in any suitable manner, e.g. by means of a Velcro fastener.

An interface for transmitting the contents of the data memory to a remote location may be provided to enhance the comfort and usability of the thermometer.

The thermometer is preferably so light and compact that it may easily be carried on the body for an extended time, even by small children.

DETAILED DESCRIPTION OF PREFERRED EMBODIMENTS

Figure 1:
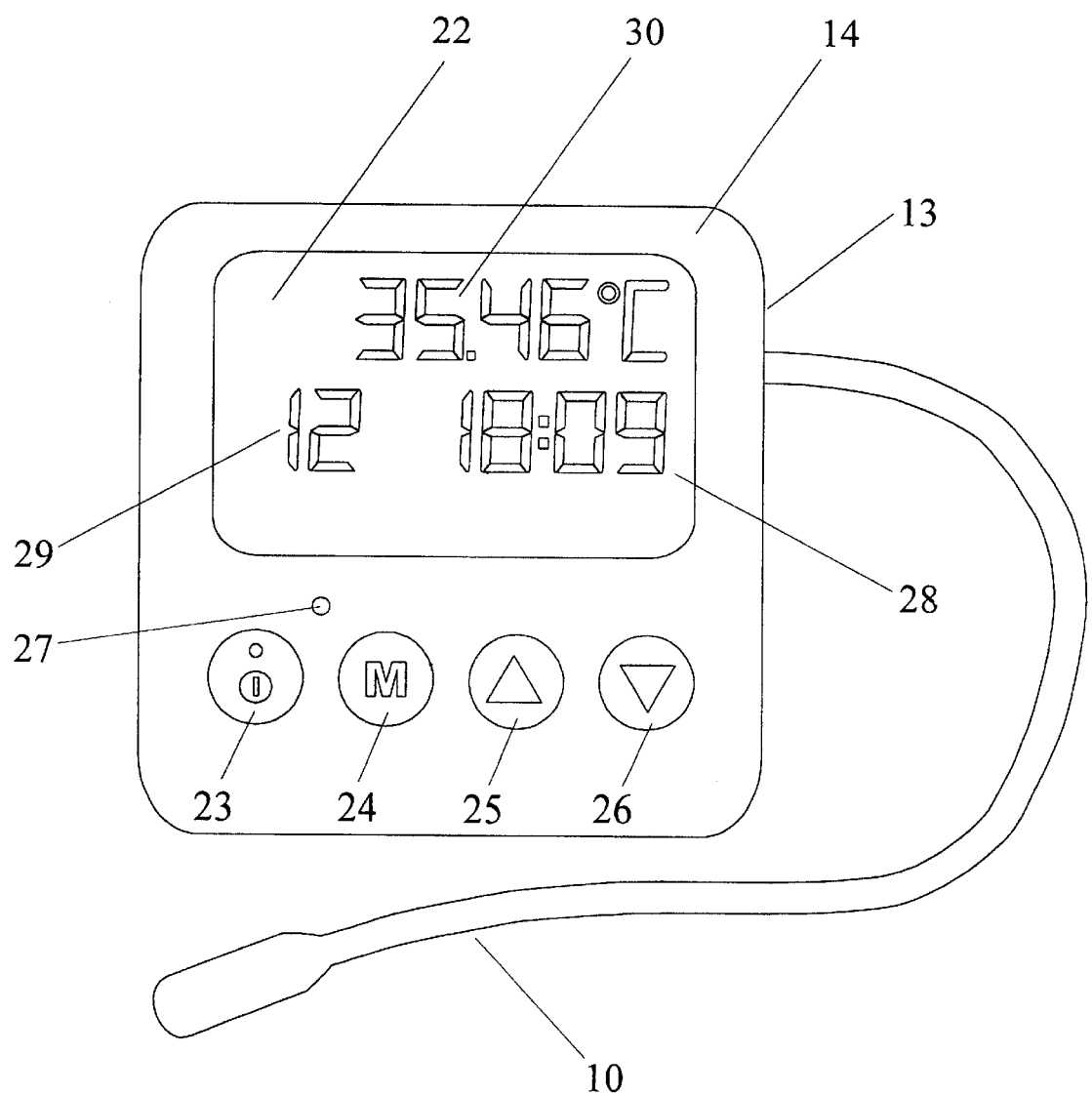
FIG. 1 shows the outside of the thermometer in accordance with an embodiment of the invention.
Figure 2:
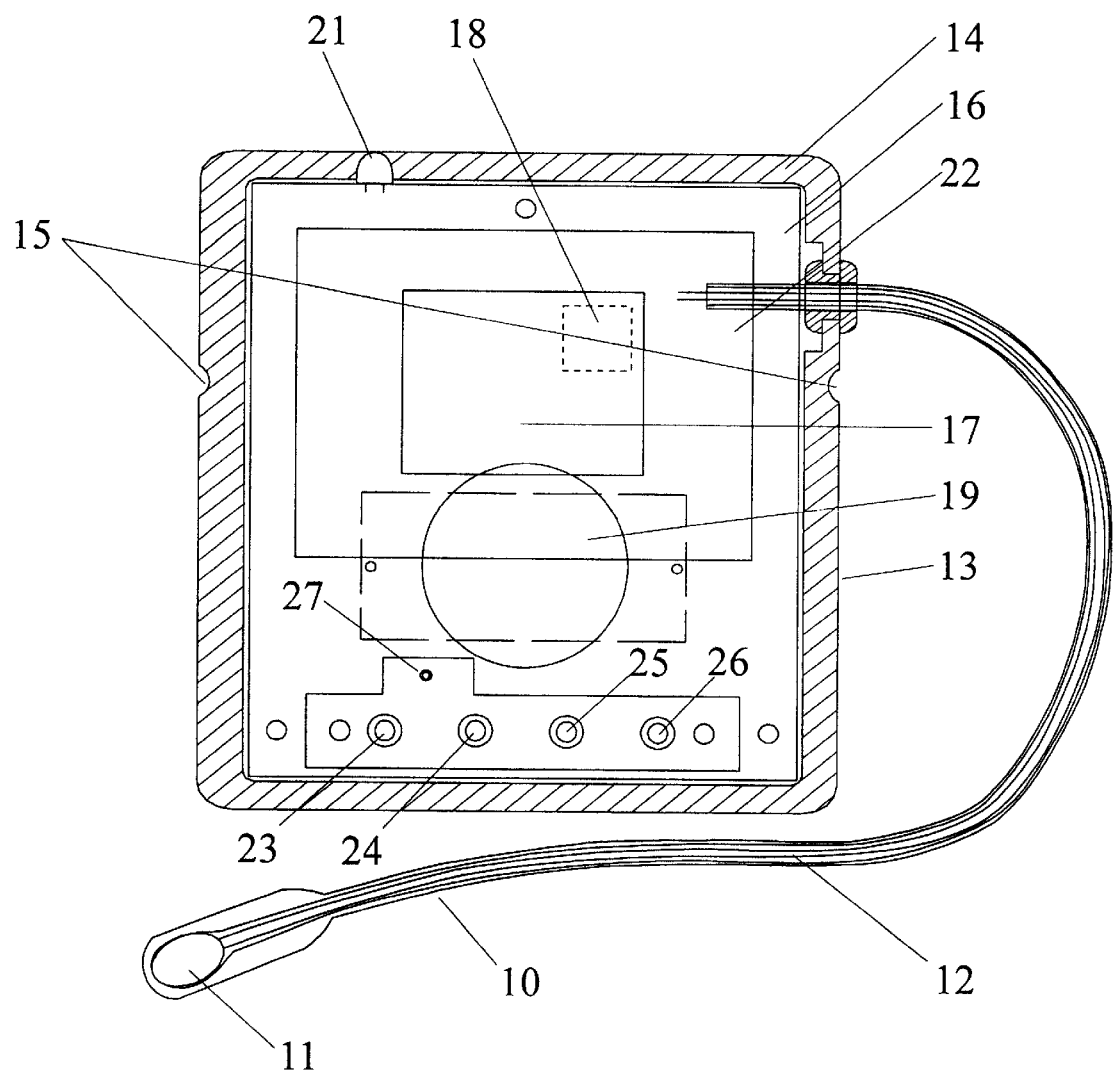
FIG. 2 is a cross-section showing the principal structure of the thermometer.
Figure 3:
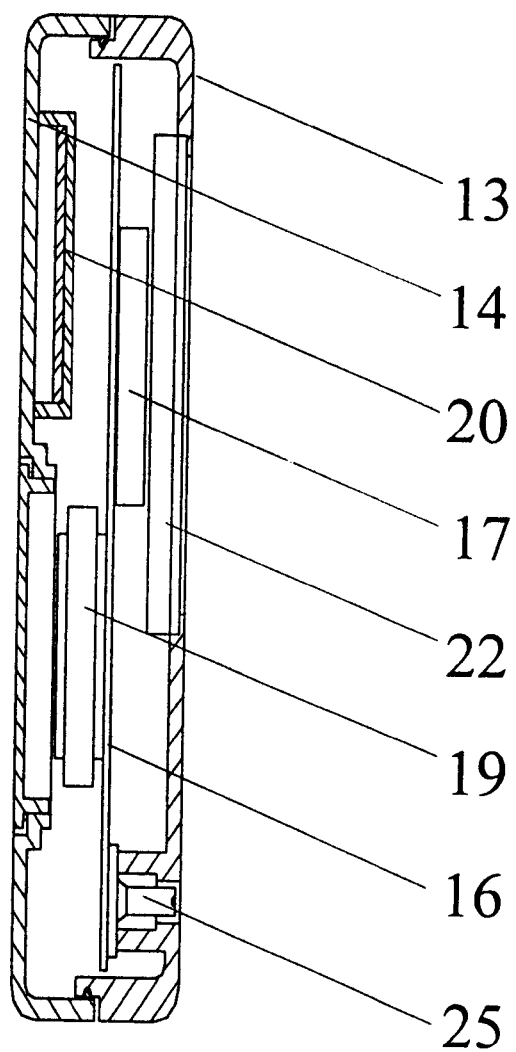
FIG. 3 is a longitudinal section of the arrangement shown in FIG. 2.

As shown in the drawings, the clinical thermometer consists of a temperature sensor 10 and an electronic measuring circuit 13. The temperature sensor 10, which is constituted by a temperature detector 11 and a cable 12, is shaped so that it permits measurements to be taken inguinally, axillarily or orally.

For continual temperature measurements to be taken from sick small children and babies, the measuring cirucit 13 is fixed externally on the belly side of the diaper, and the temperature sensor 10 is placed inside the diaper so that it can detect the inguinal temperature. For fixing, a suitable mounting adapter with a Velcro strip or clip (not shown) is selected from thermometer accessories and inserted into adapter receiving grooves 15 provided on the housing 14 of the measuring circuit 13.

The measuring circuit 13 includes, on a circuit board 16 provided inside the housing 14, a micro controller 17 with an integrated data memory 18, a battery 19, an acoustic signal generator 20 and an interface 21 for connection to a personal computer or a telemetry device; on the upper side of the housing it further has a display section 22 with various displays, input switches 23 to 26 which are accessible from the upper side, and a recessed safety switch 27.

A clock provided in the micro controller 17 drives a time display 28 on the display section 22 such that the actual time is displayed even when the thermometer is turned off. This facilitates the use of the thermometer because the user does not have to set the time.

When the thermometer is turned on by means of the on/off switch 23, the actual temperature is displayed in a temperature display 30 and a number representing the day of measurement is displayed in a day display 29 of the display section 22.

The thermometer starts taking measurements at a rate of 1/s. This enables the user to recognise immediately that the thermometer is functioning. After a period of 15 min, the measuring rate is automatically changed to a smaller value of 1/min, to save energy.

The mode switch 24 allows selecting one of a number of setting levels. On the individual levels, values are changed or functions are initiated by means of up and down switches 25, 26. The following seven levels are provided:

1. Normal measuring mode.
2. Time.
3. Alarm 1.
4. Alarm 2.
5. Storage rate (standard: 1 h).
6. Data transmission.
7. Clear.

The clock may be reset by means of the function switches 24 to 26 at any time, for instance after a change of the battery 19. Executing the clear command will clear the data memory 18 and reset the day counter.

The alarm temperatures and the storage rate of the thermometer can be set in accordance with the patient's own discretion or medical advice; for example, lower alarm temperature: 35.0° C., upper alarm temperature: 37.5° C., storage rate: 1/h. With this setting, the signal generator 20 is actuated when the child's body temperature falls below 35° C., e.g. because the blanket no longer covers the child. The alarm is also actuated when the thermometer is removed from the measuring location due to uncontrolled movements of the child. The acoustical signal generator 20 is further actuated when the child's temperature rises above 37.5° C. due to illness.

Remote monitoring of the child's body temperature is possible by means of room monitoring devices (baby phones) which are widely used nowadays. The child's parents are acoustically alarmed when a dangerous situation occurs. The signal generator 20 may be so structured that it generates an optical signal instead of, or in addition to, an acoustical signal.

A signal will also be generated when the voltage of the battery 19 falls below a critical value and change of the battery becomes necessary to maintain the monitoring function.

At the selected storing rate of 1/h, the last detected temperature value is recorded every hour along with the measuring time and day number. The recorded data sets, including temperature, measuring time and day number, may be displayed at any time by means of the up and down switches 25 and 26.

It is likewise possible to transmit the detected data to a personal computer via the interface 21, which is preferably formed as an infrared interface. The measured temperature curve may be graphically displayed on the computer and may be further transmitted, e.g. by e-mail, for examination by a physician.

The safety switch 27 serves to prevent inadvertent turning off of the thermometer or resetting, e.g. the values of the alarm temperatures. When the switch 27 has been actuated, the thermometer no longer responds to actuations of the on/off switch 23 and the mode switch 24, whereas the temperature display 30 and the time display 28 remain active. The stored measuring values also remain available for display by pressing the up and down switches 24, 25.

Convulsions caused by fever can occur not only with babies but also with children up to the age of six or more years. Since such convulsions may occur at any time, the body temperature must be monitored continuously.

With diaper wearing children, the thermometer is applied as described above. For older children, the thermometer can be mounted at the outer side of their pants by means of a clip, with the sensor being placed at the inguen. As another possibility, the thermometer may be carried in a holster on the chest. This permits placing the temperature sensor 10 in the axilla, where it is fixed by means of a special tape (with a skin compatible adhesive).

When the temperature suddenly exceeds the set alarm temperature, an alarm is generated. The child or another person nearby may then take suitable measures to prevent a convulsion or call for qualified help (emergency doctor).

A problem often occurring with older persons in need of care resides in malfunctions of the body's own temperature regulation. Dangerous hypothermia may then occur. To avoid such accidents, the body temperature may be continuously monitored by means of the thermometer. Signal transmission to nursing personnel may be done with the aid of a room monitoring device (baby phone). Suitable measuring locations are at the inguen or in the axilla.

The thermometer is switched over from a continually measuring monitoring thermometer to a maximum thermometer by setting the storage rate to zero. In the latter operation mode, the thermometer may be used for recording the basal temperature. As a special feature of this mode, any alarm values set are not monitored. If a plurality of measurements are taken on the same day, only the highest temperature value measured will be recorded. In this way, it is possible to repeat a faulty measurement without distorting the temperature curve by duplicate measurements on the same day. The measured temperature value is recorded along with the time and day number. The evaluation of the measured temperature curve may be done either manually by simply copying the measured results into a table or, more comfortably, by transmitting them to a personal computer.

The clinical thermometer with its storage rate set to zero may also be used at a normal clinical thermometer.

Possible applications for the clinical thermometer are in hospitals, in monitoring babies or in the post-operative monitoring of patients.

What is claimed is:

1. A clinical thermometer having a housing, a temperature sensor connected to said housing, a measuring circuit disposed in said housing and including a micro controller and a data memory for recording the temperature value measured by said temperature sensor, said data memory having a storage rate, a voltage supply for powering said measuring circuit, a mode switch for switching the storage rate of said memory between a continuous operation mode, in which the temperature of a measurement location is continuously monitored, and a discontinuous operation mode, in which individual temperature measurements are recorded, and switching means for selecting the storage rate at which temperature measurement values taken in said continuous operation mode are entered into said data memory.

2. The thermometer of claim 1, wherein said storage rate is adapted to be set to zero for said discontinuous operation mode.

3. The thermometer of claim 2, which in said discontinuous operation mode operates as a maximum thermometer.

4. The thermometer claim 1, further including an on/off switch, and a safety switch for locking said on/off switch and said mode switch.

5. The thermometer claim 1, further including a day display.

6. The thermometer claim 1, wherein said micro controller provides two independently adjustable alarm temperatures, said thermometer further including a signal generator adapted to be actuated by either one of said alarm temperatures.

7. The thermometer of claim 6, wherein said signal generator is an acoustical signal generator.

8. The thermometer of claim 6, wherein said signal generator is an optical signal generator.

9. The thermometer of claim 6, wherein said micro controller includes means for automatically and periodically performing a reference measurement and actuating said signal generator when the result of said reference measurement deviates from a standard value.

10. The thermometer of claim 6, wherein said micro controller actuates said signal generator when the voltage of said voltage supply falls below a critical value.

11. The thermometer of claim 1, wherein said temperature sensor is integrated in a flexible water-tight cable connected to said housing.

12. The thermometer of claim 1, further including means provided on said housing for receiving a mounting adapter.

13. The thermometer of claim 1, further including an interface for transmitting the contents of said data memory to a remote location.

* * * * *